United States Patent [19]

Nielsen et al.

[11] 4,152,211

[45] May 1, 1979

[54] IRON CONTAINING CELL MASS GLUCOSE ISOMERASE PREPARATION

[75] Inventors: Tage K. Nielsen, Herlev, Denmark; William Carasik, Ridgewood, N.J.; Lena E. Zittan, Kokkedal; Keith Gibson, Vaerløse, both of Denmark

[73] Assignee: Novo Industri A/S, Denmark

[21] Appl. No.: 827,030

[22] Filed: Aug. 23, 1977

[51] Int. Cl.$^2$ .............................................. C07G 7/02
[52] U.S. Cl. ........................................ 195/63; 195/68; 195/31 F
[58] Field of Search .......................... 195/63, 68, 31 F

[56] References Cited

U.S. PATENT DOCUMENTS

| 3,935,069 | 1/1976 | Long | 195/31 F |
|---|---|---|---|
| 3,982,997 | 9/1976 | Eaton et al. | 195/31 F |
| 4,008,124 | 2/1977 | Fujita et al. | 195/31 F |
| 4,026,764 | 5/1977 | Hurst | 195/31 F |
| 4,113,565 | 9/1978 | Hurst | 195/31 F |

*Primary Examiner*—Lionel M. Shapiro
*Attorney, Agent, or Firm*—Fidelman, Wolffe & Waldron

[57] ABSTRACT

Iron activation of cell mass of glucose isomerase preparations carried out by direct incorporation of 0.05–2.0% w/w dry basis of iron as a solid water soluble non-toxic iron salt.

Preferred compositions are dry state particulate glucose isomerases containing 0.05–2.0% iron, 0.5–3.0% magnesium oxide, and 2–15% dextrose monohydrate all w/w.

8 Claims, No Drawings

IRON CONTAINING CELL MASS GLUCOSE ISOMERASE PREPARATION

This invention relates to an iron containing glucose isomerase composition and more particular to a glucose isomerase particle form composition containing from 0.050–2.0 wt% of iron, incorporated as an iron salt therein.

A basic difficulty facing this art is that the glucose isomerase enzyme seemed to require cobalt ions in the syrup, yet cobalt is widely considered to be a toxic substance and therefore the cobalt level present in the product iso-syrup must be reduced to the parts per billion level, e.g. by ion exchange from the iso-syrup product. Heretofore the approach employed by the applicants herein and their co-workers has been to adjust processing conditions so that cobalt ions need not be present in the feed-syrup for enzyme activation purposes. As an example to this approach, reference is made to U.S. Pat. No. 4,025,389.

Recently it has been discovered that iron can be employed to activate the glucose isomerase enzyme. In U.S. Pat. No. 4,008,124 the suggestion is made to include small quantities of an iron salt in the feed-syrup for enzyme activation purposes. The same patent contains an allusion to doping the enzyme with iron during an enzyme pre-treatment step, but then suggests also maintaining some iron salt in the feed-syrup for reason that iron ion attached to the glucose isomerase is removed from the reaction mixture in conjunction with the isomerized product, especially in a continuous process.

As a practical matter, using iron as the activating metal in glucose isomerase preparations represents a significant advance in the art, because iron in small quantities is recognized to be a non-toxic material. The iron salt added to the syrup can, of course, be of food grade quality. Accordingly, the fear of leaving toxic substances in the product syrup disappears. A few parts per million of iron salt in the product is permissible.

Nonetheless, introduction of soluble iron salts into the glucose syrup feed-stream is easier to suggest than to practice. For one thing the operator of the glucose isomerization system must have a reasonable degree of chemical sophistication, and the system itself should be sophisticated. The iron salt must be metered into the glucose syrup. Chemical analysis of the glucose syrup entering the isomerization reactor for its iron content must be made periodically, if only as a cross check against satisfactory operation of the metering equipment. Secondly, since the iron binding capacity of the enzyme is either negligible or at the most limited, the point of saturation is likely to be reached during a long run isomerization process. In either case leakage of iron into the product stream will commence at some point during the process. The presence of iron in the product may induce color formation to an extent which would necessitate its removal, e.g. by ion exchange, and thus add to the costs of purification. In total, addition of iron salts to the glucose syrup is a bit of nuisance. Provision of an enzyme product having iron incorporated therein would be more advantageous, particularly if the iron were retained for the useful life of the enzyme and remained so firmly bound that practically no iron leakage would occur.

The object of this invention is to provide glucose isomerase in particulate form wherein the preparation contains from 0.05–2% by weight (dry basis) of iron, incorporated therein as a non-toxic, water soluble iron salt.

GENERAL DESCRIPTION OF THE INVENTION

Glucose isomerase is an intracellular enzyme which need not be isolated from the microorganism cells to produce an active enzyme product as witness the procedures described in U.S. Pat. Nos. 3,821,086, 3,779,869, 3,980,521 and others. All such preparations use the microoganism cell, whole or disrupted, as basis for the glucose isomerase product. The terms cell mass preparation, and cell mass particulate form are employed herein to define preparations and particles formed or otherwise fabricated from the substance of the microorganism cells along with organic reactants e.g. glutaraldehyde, proteins or agglomerating agents e.g. polyelectrolytes. On a weight basis the glucose isomerase content of cell mass preparations is a very small fraction of the preparation as a whole.

It has now been discovered that cell mass glucose isomerase preparations can bind therein substantial proportions of iron, and, moreover, relatively little of the iron is lost through extended contact with glucose and glucose-fructose syrups. The quantity of iron incorporable into cell mass preparations far exceeds the activation requirements of the glucose isomerase.

In particular non-toxic water soluble salts of iron in solid form can be mixed incorporated into the cell mass preparation during forming thereof, e.g. just prior to extrusion of a particulate form.

In addition this invention encompasses as a product the dry cell mass enzyme preparation with a non-toxic water soluble iron salt incorporated therein in iron amounts of from 0.05–2.0% w/w of the cell mass preparation. More iron can, of course, be present but no useful purpose would be served thereby.

In all instances, once the iron is incorporated within the cell mass preparation in from 0.05%–2.0% wt/wt dry weight basis, little if any of the iron is lost to the syrup over the useful life of the preparation for glucose isomerization purposes. Indeed the iron containing enzyme preparation can strip iron from the syrup. For example, the syrup entering a reactor with 4 ppm of iron might leave the isomerization reactor with an iron content of less than 1 ppm in the syrup.

In practice it has been found that improvement in productivity and/or stability of the glucose isomerase occurs when other solid ingredients are also admixed into the enzyme preparation. In particular, the initial pH drop which occurs during a period of 1–2 days after loading a column with fresh enzyme has caused some problems. A decrease in pH of the column is undesirable because it induces shrinkage of the enzyme bed which in turn may lead to bed channeling. In addition, a decrease in activity and, in severe cases, a lower stability of the enzyme product may ensue. Incorporation of 0.5–3.0% by weight of magnesium oxide into the cell mass preparation has been found to overcome the initial pH drop to a substantial degree, thus affording relatively stable syrup outlet pH values.

In addition, the admixture of solid glucose (e.g. glucose monohydrate), serving principally as a mixing aid diluent, to the cell mass preparation in amounts of 2–15% by weight (dry basis) has been found desirable.

PREFERRED EMBODIMENTS OF THE INVENTION

The preferred glucose isomerase particles contemplated herein are the glutaraldehyde reacted homogenized cell preparations disclosed in U.S. Pat. No. 3,980,521.

In the preferred mode, the water soluble iron salt is admixed with the magnesium oxide and the glucose, and then added to the cell mass before the extrusion step that forms the final granulate.

Although practice of this invention contemplates incorporation of any non-toxic water soluble iron salt into the cell mass enzyme preparation certain iron salts are preferred, namely:

| | |
|---|---|
| Ferric sulphate | Ferrous sulphate |
| Ferric chloride | Ferrous lactate |
| Ferric citrate | Ferrous citrate |
| Ferric ammonium citrate | Ferrous acetate |
| Ferric nitrate | |
| Ferric pyrophosphate | |

For further understanding of the practice of this invention, reference is made to the specific examples which follow.

In the examples the following terminology is used:

Definition of Activity

The unit of activity is defined as the amount of enzyme which forms fructose at an initial rate of 1 $\mu$mol of fructose per min. at a given set of isomerization conditions.

Assay of Activity

The activity is determined under the following conditions:

| | |
|---|---|
| Syrup | 40% w/w dissolved dextrose |
| pH inlet | 8.5 |
| Mg++ | 0.004 M |
| Temperature | 65° C. |
| Column diameter | 2.5 cm |
| - height | 35 cm |
| Flow direction | downflow |

Activity determination according to this method is expressed in IGIC units per g.

Half Life

In long run isomerizations the activity decay curves are fitted to exponential decay models of the form $$Act = A_o \times e^{-b \times t}$$

where
t is No. of hours after start of isomerization
Act is the activity of t=t
$A_o$ is the activity at t=0
and b is the decay constant in hrs$^{-1}$
from this equation half life is defined as $$T_{\frac{1}{2}} = \frac{\ln 2}{b}$$

and is given in hours.

Productivity

Productivity is defined as kg of dextrose d.s. converted to a mixture of 45% fructose and 55% glucose per kg of enzyme after a given time of isomerization.

In the examples the productivity is calculated according to an equation of the above given form after an isomerization time of $2 \times T_{\frac{1}{2}}$.

Iron

The iron content is determined according to the o-phenanthroline method (Nordisk Metodik Komite for Levnedsmidler Nr. 22, 1955 U.D.C. 664.7: 546.72).

Color

The color is determined according to the CIRF method.

Color Stability

Color stability is determined after 1 hour heating at 100° C. at pH 4.2 (CIRF).

Magnesium oxide employed was heavy type ER/B from Pharmelko, Milan, Italy.

Example 1: Addition of Ferric Citrate, Ferrous Lactate and Ferric Sulphate in Connection with Magnesium Oxide and Dextrose; Addition of Ferric Oxide A filter cake was produced according to example V in U.S. Pat. No. 3,980,521.

The cake was granulated by means of an oscillating granulator equipped with a screen with 1 cm holes.

The coarse granulate contained about 76% of water (measured by drying at 105° C.). It was divided into 6 lots.

(+) A. 8.5 kg of the coarse granulated filter cake was extruded by means of an axial extruder equipped with a screen with holes of a diameter of 0.8 mm. The extrudate was dried in a fluid bed with 60°–65° C. air to a water content of about 10%.

B. To 8.5 kg of the coarse granulated filter cake was added a mixture of 20 g of magnesium oxide, 85 g dextrose monohydrate and 40 g of ferric citrate with an iron content of 16%. After thorough mixing the mixture was extruded and dried as in A.

C. 8.5 kg of the coarse granulate was mixed with a mixture of 20 g magnesium oxide, 85 g dextrose monohydrate and 40 g ferrous lactate with an iron content of about 19%. After thorough mixing, the mixture was extruded and dried as in A.

D. 8.5 kg of the coarse granulate was mixed with a mixture of 20 g of magnesium oxide, 85 g dextrose monohydrate and 30 g ferric sulphate with an iron content of about 20%. After thorough mixing, the mixture was extruded and dried as in A.

(+) E. 8.5 kg of the coarse granulate was mixed thoroughly with a mixture of 20 g magnesium oxide and 85 g dextrose monohydrate. The mixture was extruded and dried as described under A.

(+) F. 8.5 kg of the coarse granulate was mixed thoroughly with 25 g ferric oxide containing about 58% of iron. The mixture was extruded and dried as in A.

(+) comparative example

The preparations were sieved to between 0.35 mm and 1.0 mm and the products analysed.

The pH was measured in the syrup outlet stream in samples taken after 20 hours and 43 hours, respectively.

Before the pH determination the samples were cooled to 25° C.

Table I

| Preparation | Activity Found IGIC/g | Activity Corrected IGIC/g | % gain | pH in outlet syrup after 20 hrs. | pH in outlet syrup after 43 hrs. |
|---|---|---|---|---|---|
| +A | 246 | 246 | 0 | 6.68 | 7.62 |
| B | 307 | 326 | 33 | 7.99 | 8.20 |
| C | 296 | 315 | 28 | 7.60 | 7.98 |
| D | 308 | 328 | 33 | 7.90 | 8.14 |
| +E | 254 | 267 | 8 | 7.99 | 8.20 |
| +F | 257 | 260 | 6 | 6.86 | 7.65 |

As can be seen from Table I, only addition of soluble iron components gives activity gain of any importance. Addition of ferric oxide gave only about 6% compared to about 30% for the soluble salts.

Example II: Addition of Magnesium Oxide+Dextrose and Magnesium Oxide+Dextrose+Iron Salt A filter cake was produced according to example V in U.S. Pat. No. 3,980,521. The cake was granulated by means of an oscillating granulator equipped with a screen with 1 cm holes.

The coarse granulate contained about 79% of water. It was divided into 5 lots of 8.5 kg.

(+) A. 8.5 kg was extruded and dried as in example 1A without addition of additives.

(+) B. To 8.5 kg granulated filter cake was added 25 g magnesium oxide. After thorough mixing it was extruded and dried as in A.

(+) C. To 8.5 kg granulated filter cake was added 25 g magnesium oxide and 200 g dextrose monohydrate. After mixing it was extruded and dried as in A.

(+) D. To 8.5 kg granulated filter cake was added a mixture of 25 g magnesium oxide and 300 g dextrose. After mixing it was extruded and dried.

E. 8.5 kg of the filter cake was mixed with a mixture of 25 g magnesium oxide, 200 g dextrose monohydrate and 40 g ferric sulphate containing about 20% iron. Thereafter it was extruded and dried.

(+) Comparative example

The dried preparations were sieved to between 0.35 mm and 1.0 mm and the products analysed.

The pH in the outlet syrup was measured in samples taken after 20 hours and 43 hours, respectively, and cooled to 25° C.

Table II

| Preparation | % added material | Activity IGIC/g Found | Activity IGIC/g Corrected for added inact. mat. | % gain | pH in outlet syrup after 20 hrs. | pH in outlet syrup after 43 hrs. |
|---|---|---|---|---|---|---|
| +)A | 0 | 220 | 220 | 0 | 6.85 | 7.40 |
| +)B | 1 | 222 | 224 | 2 | 8.18 | 8.23 |
| +)C | 10 | 216 | 240 | 9 | 8.14 | 8.22 |
| +)D | 14 | 216 | 251 | 14 | 8.15 | 1.21 |
| E | 12 | 272 | 309 | 40 | 8.15 | 8.27 |

As can be seen from Table II, only addition of an iron salt affords a significant increase in activity.

Example III: Addition of Ferric Citrate, Ferric Pyrophosphate, Ferric Ammonium Citrate and Ferrous Sulphate A coarse granulated filter cake with about 76% of water as in example 1 was divided into 6 lots of each 8.5 kg.

(+) A. 8.5 kg granulated filter cake was extruded and dried as in example 1 to give a reference composition.

B. To 8.5 kg of the coarse granulate was added a mixture of 25 g magnesium oxide, 25 g ferric citrate with about 16% of iron and 250 g dextrose monohydrate. After thorough mixing the granulate was extruded and dried as in A.

C. 8.5 kg of the coarse granulate was extruded and dried as in A after addition of 25 g magnesium oxide, 50 g ferric citrate and 250 g dextrose monohydrate.

D. 8.5 kg of the coarse granulate was treated as C except that the 50 g ferric citrate was replaced by 30 g ferric pyrophosphate with an iron content of about 12%.

E. To 8.5 kg of the coarse granulate was added 25 g magnesium oxide, 250 g dextrose monohydrate and 30 g ferric ammonium citrate with an iron content of about 15%. After thorough mixing the granulate was extruded and dried as in A.

F. To the last lot of 8.5 kg was added 25 g magnesium oxide, 250 g dextrose monohydrate, and 30 g ferrous sulphate with an iron content of about 30%. After thorough mixing the granulate was extruded and dried as in A.

(+) Comparative example

The dried preparations were sieved to between 0.35 and 1.0 mm and the products obtained were analysed. The pH of the outlet syrup was measured after 20 and 43 hours.

Table III

| | Activity IGIC/g Found | Activity IGIC/g Corrected | % gain | pH in outlet syrup after 20 hrs. | pH in outlet syrup after 43 hrs. |
|---|---|---|---|---|---|
| +)A | 229 | 229 | 0 | 6.64 | 7.25 |
| B | 261 | 293 | 28 | 7.90 | 8.24 |
| C | 273 | 306 | 34 | 7.84 | 8.22 |
| D | 266 | 299 | 31 | 7.79 | 8.19 |
| E | 268 | 301 | 31 | 7.70 | 8.14 |
| F | 263 | 295 | 29 | 7.87 | 8.03 |

No significant difference in activating effect of the applied iron salts is observed.

(+) Example IV: Effect of Magnesium Oxide Incorporation on pH Drop, Activity and Stability (+) Comparative example a. Three enzyme preparations were produced according to the same procedure as described in Example I. To the coarse granulated filter cake was added magnesium oxide in sufficient amounts to give preparations with the following magnesium oxide content in the final dried preparations.

Prep. B1 no additive
- B2 2% magnesium oxide
- B3 5% magnesium oxide

Isomerizations were performed in 60 ml jacketed glass columns (h×d=35×1.5 cm) using 15 grams of each of the three preparations. The parameters for isomerization were:

| Syrup | 45% w/w redissolved dextrose |
|---|---|
| pH inlet | 8.0 ± 0.1 |
| Mg add. to syrup | 0.0008 M |
| Temperature | 65° C. |

An inlet pH of 8.0 is lower than the one normally used and regarded as optimum, but here it was applied to screen the effect of magnesium oxide addition.

The isomerizations were continued until the preparations had decreased in activity to an arbitrarily chosen activity of 20–25 μmol/min/g.

The following results were obtained:

Table IV (a) i

| Preparation | Max. measured activity/after hours | Running time, hrs. | Half life hours | Productivity after 2 × T½ |
|---|---|---|---|---|
| B1 | 88/72 | 665 | 257 | 369 |
| B2 | 143/16 | 665 | 238 | 436 |
| B3 | 124/16 | 378 | 161 | 253 |

Outlet pH values were found as tabulated below.

Table IV (a) ii

| Preparation | 0 (soaking) | 17 | 42 | 70 | 140 | 230 | 350 | 665 |
|---|---|---|---|---|---|---|---|---|
|  | — | 6.2 | 6.2 | 6.1 | 6.0 | 6.0 | 5.9 | 6.3 |
| B2 | 8.4 | 7.4 | 7.0 | 6.7 | 6.4 | 6.2 | 6.2 | 6.9 |
| B3 | 9.3 | 8.6 | 7.7 | 7.2 | 6.7 | 6.4 | 6.3 | — |

The results demonstrate that addition of 5% magnesium oxide gives rise to high initial outlet pH's. This appears to influence the max. observed activity as well as the stability and productivity in descending direction.

In this test, isomerizing with an inlet pH of 8.0, a higher max. activity and productivity resulted from presence of 2% added magnesium oxide as compared to no additives.

b. To optimize the addition of magnesium oxide four additional preparations were produced according to the procedure described in Example I. The additive contents of the dried preparations were:

A no magnesium oxide
B ½% magnesium oxide + 9% dextrose
C 1% magnesium oxide + 9% dextrose
D 2% magnesium oxide + 9% dextrose Isomerizations were performed in 60 ml jacketed glass columns (h×d = 14 × 1.5 cm) using the following parameters:

| Syrup | 45% w/w redissolved dextrose |
|---|---|
| pH inlet | 8.4 ± 0.1 |
| Mg add. to syrup | 0.0016 M |
| Temperature | 65° C. |

The isomerizations were continued for 351 hours. The following results were obtained:

Table IV (b) i

| Preparation | Max. measured activity/after hours | Activity after 351 hours | Productivity after 351 hours |
|---|---|---|---|
| A | 103/67 | 79 | 397 |
| B | 105/18 | 75 | 384 |
| C | 103/18 | 72 | 371 |
| D | 98/18 | 65 | 354 |

Outlet pH values were measured as seen from the table:

Table IV (b) ii

| Preparation | 19 | 43 | 67 | 140 | 210 | 303 |
|---|---|---|---|---|---|---|
| A | 6.6 | 6.7 | 7.0 | 7.3 | 7.4 | 7.2 |
| B | 7.1 | 7.0 | 7.3 | 7.5 | 7.5 | 7.1 |
| C | 7.4 | 7.6 | 7.7 | 7.6 | 7.6 | 7.2 |

Table IV (b) ii-continued

| Preparation | 19 | 43 | 67 | 140 | 210 | 303 |
|---|---|---|---|---|---|---|
| D | 8.4 | 8.0 | 7.8 | 7.6 | 7.5 | 7.2 |

The results indicate no great differences in activity, stability, or productivity between the four preparations. Outlet pH's are influenced. Addition of 1% magnesium oxide gives almost constant outlet pH during the run and is therefore the preferred level of addition. Both ½ and 2% magnesium oxide addition have effect on the outlet pH compared to the control, but in both cases some pH variation during the first 150 hours was found.

Example V: Isomerization Experiments

A coarse granulated filter cake prepared according to U.S. Pat. No. 3,980,521 Example V was used for the following preparations. The filter cake contained about 77% water. (+) 410/A. No addition.

(+) 410/B. About 10 parts by weight of mix 1 were added to about 90 parts by weight on a dry basis, of the filter cake. Mix 1 consisted of dextrose (100 parts) and magnesium oxide (8 parts).

410/C. About 2 parts by weight of mix 2 were added to about 98 parts by weight of the filter cake dry basis. Mix 2 consisted of dextrose (100 parts), magnesium oxide (10 parts) and ferric sulphate (12 parts).

410/D. About 7 parts by weight of mix 2 were added to about 93 parts by weight of the filter cake, dry basis.

(+) 410/E. No addition.
(+) Comparative example.

The mixtures 410/A to 410/E were then extruded through a screen with 0.8 mm holes, and then dried in a fluid bed to a water content of about 10%.

The iron contents of the five final preparations were determined.

410/A—0.04%
410/B—0.03%
410/C—0.08%
410/D—0.18%
410/E—0.04%

Isomerizations were performed with material from preparations 410/A, 410/B, 410/D and 410/E, using the following conditions.

| Syrup | 45% w/w redissolved dextrose |
|---|---|
| pH inlet | 8.4 ± 0.1 |
| $Mg^{2+}$ | 0.0016 M |
| Temperature | 62° C. |
| Column dimensions | h 40 cm |
|  | d 5.8 cm |
|  | v 1 litre |
| Weight of enzyme | 260 g |

The enzyme was soaked for 2 hours at room temperature in the above described syrup, but at pH 8.0 and then packed into the column.

The following results were obtained:

Table V (a)

| Preparation | Max. measured activity | Total run time hours | pH outlet after 21h | pH outlet after 48h | pH outlet after 92h | Half life T½ hours | Productivity after 2 × T½ h. |
|---|---|---|---|---|---|---|---|
| 410/A | 158 | 1293 | 6.9 | 6.8 | 7.2 | 842 | 1880 |
| 410/B | 155 | 936 | 7.4 | 7.7 | 8.0 | 818 | 1790 |
| 410/D | 202 | 1316 | 7.3 | 7.5 | 7.7 | 843 | 2295 |

Table V (a)-continued

| Pre-para-tion | Max. meas-ured activity | Total run time hours | pH outlet after 21h | pH outlet after 48h | pH outlet after 92h | Half life $T_{\frac{1}{2}}$ hours | Productivity after $2 \times T_{\frac{1}{2}}$h. |
|---|---|---|---|---|---|---|---|
| 410/E | 151 | 1147 | 6.9 | 6.9 | 7.7 | 828 | 1755 |

The concentration of iron in the outlet syrup from these columns was determined.

Table V (b)

| | Fe (ppm) in outlet syrup | | |
|---|---|---|---|
| Preparation | 2½ hours after start | 21 hours after start | 27 hours after start |
| 410/A | <1 | <1 | <1 |
| 410/B | <1 | <1 | <1 |
| 410/D | approx. 1 | <1 | <1 |
| 410/E | <1 | <1 | <1 |

A second set of isomerization experiments was performed with material from preparations 410/C, 410/D and 410/E, using the following conditions:

| | |
|---|---|
| Syrup | 45% w/w redissolved dextrose |
| pH$_2$ inlet | 8.4 ± 0.1 |
| Mg$^{2+}$ | 0.0016 M |
| Temperature | 65° C. |
| Column dimensions | h 20 cm |
| | d 2.5 cm |
| | v 100 ml |
| Weight of enzyme | 20 g |

The enzyme was soaked for one hour at room temperature in the above described syrup, and then packed into the column.
The following results were obtained:

Table V (c)

| Pre-para-tion | Max. measured activity | Total run time, hours | pH outlet after 17h | pH outlet after 45h | pH outlet after 200h | Half life $T_{\frac{1}{2}}$ hours | Productivity after $2 \times T_{\frac{1}{2}}$ |
|---|---|---|---|---|---|---|---|
| 410/C | 210 | 900 | 7.0 | 7.8 | 8.1 | 512 | 1510 |
| 410/D | 250 | 900 | 7.5 | 8.0 | 8.2 | 484 | 1725 |
| 410/E | 190 | 900 | 6.9 | 7.4 | 8.2 | 485 | 1340 |

The concentration of iron in the outlet syrup from these columns was determined.

Table V (d)

| | Fe (ppm) in outlet syrup | | | | |
|---|---|---|---|---|---|
| Preperation | 0hrs. (soaking) | 24 hrs after start | 72 hrs after start | 140 hrs after start | 850 hrs after start |
| 410/C | 0.8 | <0.5 | <0.5 | <0.5 | <0.5 |
| 410/D | 3.6 | <0.5 | <0.5 | <0.5 | <0.5 |
| 410/E | <0.5 | <0.5 | <0.5 | <0.5 | <0.5 |

The CIRF color of the outlet syrup from these columns was determined.

Table V (e)

| | CIRF color in syrup | | |
|---|---|---|---|
| | 0 hrs. (soaking) | 24 hrs. after start | 72 hrs. after start |
| 410/C | 0.266 | 0.030 | 0.019 |
| 410/D | 0.247 | 0.036 | 0.020 |
| 410/E | 0.232 | 0.036 | 0.022 |

For comparison, the CIRF color of three samples of the inlet syrup used during this period were measured to 0.019, 0.012 and 0.014.

The color stability of the outlet syrup from these columns was determined.

Table V (f)

| | Color stability of syrup | | |
|---|---|---|---|
| Preparation | 0 hrs. (soaking) | 24 hrs. after start | 72 hrs. after start |
| 410/C | 0.21 | 0.040 | 0.014 |
| 410/D | 0.21 | 0.050 | 0.017 |
| 410/E | 0.22 | 0.044 | 0.017 |

For comparison, the color stability of three samples of the inlet syrup used during this period was measured. The results were 0.004, 0.002 and 0.004.

The iron content of the enzyme preparations was determined before and after use.

Table V (g)

| | mg iron in column packed with 20 g enzyme | |
|---|---|---|
| Preparation | At start | After 900 hrs. |
| 410/C | 16 | 24 |
| 410/D | 36 | 42 |
| 410/E | 8 | 14 |

It will be noted that the iron content after 900 hours was greater than at the start of the experiment. Thus the enzyme adsorbed iron from the input syrup. Since, no iron was added to the input syrup used in these experiments, the iron adsorbed by the enzyme originated from the traces of iron naturally present in the solutions of crystalline dextrose. Analysis of the iron content of the 45% w/w redissolved dextrose syrup showed <0.5 ppm, and approximately 0.1 ppm iron. In the course of the 900 hours that these columns ran, approximately 75000 g of syrup were passed through each column containing 20 g enzyme. If the average iron concentration of this inlet syrup was 0.1 ppm, then the total iron content of the inlet syrup was $75000 \times 10^{-7}$ g = 7.5 mg.

This corresponds well to the amount picked up by the enzyme preparations during the course of the test.

Conclusions

Addition of magnesium oxide has a significant influence on the outlet pH in the period between 0 and 100 hours after start up. With magnesium oxide, as in 410/B and 410/D, the outlet pH was 0.5–1.0 unit higher than without magnesium oxide, as in 410/A and 410/E.

Addition of iron salt, as in 410/D, increased the activity without impairing the stability, giving rise to an overall increase in productivity of between 20 and 30%.

Addition of smaller amounts of magnesium oxide and iron salt, as in 410/C, gave a smaller increase in outlet pH and a smaller increase in productivity, but these increases were still significant.

Example VI: Comparison of Ferrous and Ferric Salts

A mixture of iron salt, dextrose, and magnesium oxide was added to samples of a coarse granulated filtercake made according to U.S. Pat. No. 3,980,521 Example V. The mixture was then further processed by extrusion through a screen with 0.8 mm holes and finally by drying in a fluid bed to a water content of approximately 10%. The composition and amount of the mix consisting of iron salt, dextrose and magnesium oxide were such as to give final preparations with the following compositions:

Table VI (a)

| Preparation | Iron salt | Dextrose | Magnesium oxide |
|---|---|---|---|
| IG 403 II C | 1.2% Ferric sulphate | 8% | 1% |
| IG 403 II D | 1.2% Ferrous sulphate | 8% | 1% |
| IG 403 II E | None | 8% | 1% |

Analysis of the preparations gave the following results for the actual Fe content:
IG 403 II C 0.22%
IG 403 II D 0.27%
IG 403 II E 0.05%

Isomerizations were performed under the following conditions:

| Syrup | 45% redissolved dextrose |
|---|---|
| pH inlet | 8.4 ± 0.1 |
| $Mg^{++}$ | 0.0016 M |
| Temperature | 65° C. |
| Column dimensions | h 20 cm |
|  | d 2.5 cm |
|  | v 100 ml |
| Weight of enzyme | 20 g |

The enzyme was soaked for one hour at room temperature in the above described syrup and then packed into the column.

The following results were obtained:

Table VI (b)

| Preparation | Max. measured activity | Total run time, hours | Half life $T_{\frac{1}{2}}$, hours | Productivity after $2 \times T_{\frac{1}{2}}$ |
|---|---|---|---|---|
| IG 403 II C | 290 | 755 | 482 | 2093 |
| IG 403 II D | 274 | 755 | 467 | 1914 |
| IG 403 II E | 254 | 755 | 431 | 1635 |

The iron contents of the enzyme preparations were determined before and after use.

| | mg Fe in column packed with 20 g enzyme | |
|---|---|---|
| Preparation | at start | after 755 h |
| IG 403 II C | 44 | 52 |
| IG 403 II D | 54 | 68 |
| IG 403 II E | 10 | 16 |

Again the iron content increased slightly during the course of the test, indicating that the preparations adsorbed iron from the traces of iron present in the redissolved dextrose syrup.

Conclusion

Addition of either ferrous or ferric sulphate increased the activity and productivity of the enzyme preparation.

Example VII: Demonstration of Iron Saturation

A coarse granulated filter cake according to U.S. Pat. No. 3,980,521 Example V was used for the following preparations:
415/A—No addition
415/B—About 10 parts by weight of mix 2 were added to about 90 parts by weight of the filter cake on a dry weight basis. The filter cake contained approximately 77% water. Mix 2 consisted of dextrose (100 parts), magnesium oxide (10 parts) and ferric sulphate (12 parts).

The mixtures 415/A and 415/B were then extruded through a screen with 0.8 mm holes and then dried in a fluid bed, to a water content of about 10%.

The iron contents of the two final preparations were determined:
415/A—0.03%
415/B—0.26%

Isomerizations were performed with preparations 415/A and 415/B using the following conditions:

| Syrup | 45% w/w redissolved dextrose |
|---|---|
| pH inlet | 8.3 ± 0.1 |
| Mg | 0.0016 M |
| Fe | 0.00007 M (4 ppm) |
| Temperature | 65° C. |
| Column dimensions | h 20 cm |
|  | d 2.5 cm |
|  | v 100 ml |
| Weight of enzyme | 20 g |

The enzyme was soaked in the syrup for one hour at room temperature and then packed into the column.

The following results were obtained:

Table VII (a)

| Preparation | Max. measured activity | Time to reach max. activity, hours | Total run, time, hours | Half life $T_{\frac{1}{2}}$, hours | Productivity after $2 \times T_{\frac{1}{2}}$ h. |
|---|---|---|---|---|---|
| 415/A | 272 | 160 | 906 | 611 | 2560 |
| 415/B | 275 | 20 | 906 | 547 | 2260 |

The concentration of iron in the outlet syrup from these columns was determined.

Table VII (b)

| | Fe (ppm) in outlet syrup at | | | | |
|---|---|---|---|---|---|
| Preparation | 0 hours (soaking) 20 hrs. | 70 hrs. | 350 hrs. | 900 hrs. | |
| 415/A | <0.5 | <0.5 | <0.5 | <0.5 | 0.5 |
| 415/B | 7 | <0.5 | <0.5 | <0.5 | 0.6 |

The iron contents of the enzyme preparations were determined before and after use.

| | mg iron in column packed with 20 g enzyme | |
|---|---|---|
| Preparation | at start | after 900 hours |
| 415/A | 6 | 320 |
| 415/B | 52 | 380 |

Conclusions

415/A gave 13% higher productivity than 415/B. However, it should be noted that 415/B contains approximately 10% by weight of non-enzyme material. Thus, calculated on the basis of the original enzyme containing filter cake, both preparations gave approximately the same productivity.

The activity of 415/A increased during the first 160 hours of the run. This is in contrast to 415/B which gave maximum activity after 20 hours. This indicates that 415/A was slowly adsorbing iron from the input syrup with a resulting slow activation. This slow activation is also the reason for the longer exponential decay half life observed for 415/A, i.e. activation and exponential decay occurred simultaneously.

During the 900 hours of the experiment about 90000 g of syrup were passed through each column containing 20 g enzyme preparation. The iron content of this syrup was 4 ppm. Thus 90000 g syrup contained 360 mg iron. The iron content of the two columns increased by 314 and 328 mg. Thus the greater part of the iron in the input syrup was removed by the enzyme preparations. The results show that after 900 hours the level of iron in the output syrup had started to increase. This suggests that the enzyme preparations were approaching the limit of their ability to absorb iron.

What is claimed is:

1. A method for iron activating a cell mass particulate form of glucose isomerase which comprises admixing therewith a solid form non-toxic water soluble iron salt, in an amount of from 0.050–2.0% w/w of iron.

2. The method of claim 1 wherein the iron salt is selected from the group consisting of ferric ammonium citrate, ferric sulphate, ferric chloride, ferric citrate, ferric pyrophosphate, ferric nitrate, ferrous sulphate, ferrous lactate, ferrous citrate and ferrous acetate.

3. The method of claim 1 wherein incorporation is through solid form admixture of glucose isomerase, iron salt and from 0.5–3.0% w/w of magnesium oxide based upon the dry weight of the glucose isomerase.

4. The method of claim 1 wherein incorporation is through solid form admixture of glucose isomerase, iron salt, from 0.5–3.0% w/w of magnesium oxide based upon the dry weight of the glucose isomerase, and from 2–15% w/w of dextrose monohydrate.

5. An iron activated cell mass dry state particulate form of glucose isomerase containing therein from 0.050–2.0% w/w of iron as a non-toxic water soluble iron salt.

6. The composition of claim 5 including therein from 0.5–3.0% w/w of magnesium oxide.

7. The composition of claim 5 including therein from 0.5–3.0% w/w of magnesium oxide and from 2–15% w/w of dextrose monohydrate.

8. The composition of claim 5 wherein the non-toxic iron salt is selected from the group consisting of ferric sulphate, ferric chloride, ferric citrate, ferric ammonium citrate, ferric nitrate, ferric pyrophosphate, ferrous sulphate, ferrous lactate, ferrous citrate and ferrous acetate.

* * * * *